United States Patent
Kosar et al.

(10) Patent No.: US 10,166,330 B2
(45) Date of Patent: Jan. 1, 2019

(54) PHARMACEUTICAL DRUG DELIVERY SYSTEM

(71) Applicant: SABANCI ÜNIVERSITESI, Istanbul (TR)

(72) Inventors: Ali Kosar, Istanbul (TR); Osman Yavuz Perk, Istanbul (TR)

(73) Assignee: SABANCI ÜNIVERSITESI, Istanbul (TR)

( * ) Notice: Subject to any disclaimer, the term of this patent is extended or adjusted under 35 U.S.C. 154(b) by 98 days.

(21) Appl. No.: 15/123,654

(22) PCT Filed: Mar. 12, 2015

(86) PCT No.: PCT/EP2015/055168
§ 371 (c)(1),
(2) Date: Sep. 5, 2016

(87) PCT Pub. No.: WO2015/136036
PCT Pub. Date: Sep. 17, 2015

(65) Prior Publication Data
US 2017/0072138 A1    Mar. 16, 2017

(30) Foreign Application Priority Data
Mar. 13, 2014 (EP) ..................................... 14159546

(51) Int. Cl.
*A61M 37/00* (2006.01)
*A61M 5/142* (2006.01)
*A61M 39/02* (2006.01)

(52) U.S. Cl.
CPC ........ *A61M 5/14212* (2013.01); *A61M 5/142* (2013.01); *A61M 5/14276* (2013.01);
(Continued)

(58) Field of Classification Search
CPC ...... A61M 37/0015; A61M 2037/0023; A61M 2037/003; A61M 2037/0046;
(Continued)

(56) References Cited

U.S. PATENT DOCUMENTS

2005/0042766 A1*  2/2005  Ohman ............... B01L 3/50273
                                                          436/174
2007/0078513 A1*  4/2007  Campbell .......... A61K 31/4353
                                                          623/1.44
(Continued)

FOREIGN PATENT DOCUMENTS

EP    1177802 B1    9/2004
EP    1432464 B1    1/2009
(Continued)

*Primary Examiner* — Kevin C Sirmons
*Assistant Examiner* — Tiffany Legette-Thompson
(74) *Attorney, Agent, or Firm* — Gokalp Bayramoglu

(57) ABSTRACT

A pharmaceutical drug delivery system having a base (1) comprising at least two inlets (2), an outlet (20) and a passive mixing chamber (7) having micro pin fins (8) with heights in the range of 10 to 100µm characterized in that the base (1) is selectively coated with nanostructures which are made of a material different than the material of said base, such that the base (1) comprises a plurality of regions $R_1$ to $R_N$ each having a different nanostructure coating intensity, and such that a surface tension gradient is established among regions $R_1$ to $R_N$ for promoting fluid flow towards the outlet (20). The present invention further proposes a method for obtaining a pharmaceutical drug delivery system.

15 Claims, 5 Drawing Sheets

(52) U.S. Cl.
CPC .............. *A61M 2039/0205* (2013.01); *A61M 2205/0244* (2013.01)

(58) Field of Classification Search
CPC ............. A61M 5/142; A61M 5/14276; A61M 5/14212; B01L 3/502
USPC ......................................................... 604/82
See application file for complete search history.

(56) References Cited

U.S. PATENT DOCUMENTS

| | | | |
|---|---|---|---|
| 2007/0100306 A1* | 5/2007 | DiZio | A61F 13/58 604/371 |
| 2009/0014360 A1* | 1/2009 | Toner | B01D 21/0087 209/208 |
| 2012/0058500 A1* | 3/2012 | Mitchell | B01L 3/502746 435/13 |
| 2012/0220980 A1 | 8/2012 | Ross | |
| 2012/0319083 A1* | 12/2012 | Lee | H01L 21/02422 257/29 |
| 2013/0027639 A1* | 1/2013 | Chien | C09K 19/02 349/84 |
| 2013/0211310 A1* | 8/2013 | Bommarito | B08B 17/06 602/48 |

FOREIGN PATENT DOCUMENTS

| | | |
|---|---|---|
| WO | WO0115985 A1 | 3/2001 |
| WO | WO2004026361 A1 | 4/2004 |
| WO | WO2007149439 A2 | 12/2007 |

\* cited by examiner

PHARMACEUTICAL DRUG DELIVERY SYSTEM

TECHNICAL FIELD OF THE INVENTION

The present invention relates to a pharmaceutical drug delivery system which has features of passive reagent mixing with enhanced micro structures and fluid flow promotion with nanostructures provided on the system surfaces. The present invention further relates to a production method for such pharmaceutical drug delivery system.

BACKGROUND OF THE INVENTION

Drugs are composed of reagents, which need to be precisely mixed and heated to generate a desired composition. In this process, the extent of mixing and heating and the dosage for each reagent are very critical.

Once a drug is produced, partial degradation is likely to occur. The pharmacokinetic facts affect the efficiency of a released drug by means of distributing the drug everywhere in the body. Patients might be given high doses of drugs than they need to take, which increases side effects of corresponding drugs. In addition, doses of each drug change from patient to patient. Moreover, conventional dosing usually depends on animal based experimental results. Due to the above reasons, compact and independent drug delivery systems suitable for a specific patient are urgently sought in the drug delivery community.

A drug delivery system (DDS) is defined as a formulation or a system that enables the introduction of a therapeutic substance in the body and improves its efficacy and safety by controlling the rate, time, and place of release of drugs in the body. This process includes the administration of the therapeutic product, the release of the active ingredients across the biological membranes to the site of action. In the literature, the most common methods of the drug delivery include deliveries through the mouth, skin, nasal, ocular, rectal, injection and inhalation routes.

Drug delivery systems use automated procedures, which can be initiated by just pushing a button. Therefore, human errors are minimized. These systems may be designed as reprogrammable systems. Therefore, application of the systems can be extended to any pharmaceutical drug preparation procedure such as preparation of radiopharmaceutical drugs. The dimensions of such system can be within the range of 0.1-1 mm.

Current efforts in the area of drug delivery consist of the improvement of targeted delivery, where the drug is only active in the targeted area of the body (for example, in cancerous tissues), sustained release formulations, in which the drug is released over a period of time in a controlled manner from a formulation, and reducing the side effects of the drugs, which are hazardous to the people's health, as much as possible.

The method used in the drug delivery system can have a significant effect on the drugs' efficiency. Some reagents have an optimum concentration range, within which utmost benefit is reached, and concentrations below this range can be toxic or produce no healing benefit at all.

To prevent harmful side-effects and to increase drug's efficiency, various drug delivery systems are currently under development. By increasing the mixing rate of the reagents of the certain drug, the improvement of the drug's efficiency and the reduction of the hazardous side effects of the drug are the main purpose of the proposed concept.

Prior art applications in the present technical field mainly disclose clinical dispensers, automated injectors and mixers. However, prior art implementations are not satisfactory for fulfilling a multifunctional task, namely heating, mixing and delivering the reagent. The international publication WO 2007149439 discloses a drug delivery dispenser, which has a feature of heating. The device uses drug cartridges and processes the reagent inside a chamber. However, from the aspect of size, the device can only be used in stable clinical operations.

In the patent publication EP1432464, a controller unit for the precise drug amount is disclosed. However this control unit is only capable of sending different signals to the chambers with different sizes, which would contain a precise amount of reagent. This feature is not realized via an electronic control circuit which would provide a safer manner for precision of drug amounts to be delivered.

The mixing feature is common among the prior art, however it was never done in a small scale and passive manner as in the present invention. EP1177802 features disposable parts and programmable flow control. Neither passive mixing nor heating features are present in the publication, which would enhance mixing rates. Moreover, it has a relatively expensive base cost since the used actuators are made of piezoelectric materials, which have a high unit price.

OBJECTS OF THE INVENTION

Primary object of the present invention is to provide a Micro Electro Mechanical System (MEMS) wherein the above mentioned deficiencies in the prior art are overcome.

Another object of the present invention is to provide a Micro Electro Mechanical System (MEMS) which is a drug delivery system featuring the homogenous mixing process of multiple reagents, the heating process, and the controllability.

Another object of the present invention is to provide a Micro Electro Mechanical System (MEMS) which is a drug delivery system wherein self-pumping of reagents without requiring any external device is provided.

Further an object of the present invention is to provide a Micro Electro Mechanical System (MEMS) which is a drug delivery system that is independent of any external power source.

Still further an object of the present invention is to provide a Micro Electro Mechanical System (MEMS) which is a drug delivery system wherein drugs are administered to patients with just sufficient amount of the reagents in a controlled and safe fashion so those unnecessary amounts of the reagents are limited in quantity.

Yet another object of the present invention is to provide an autonomous, effective, and compact Micro Electro Mechanical System (MEMS) which is a drug delivery system.

SUMMARY OF THE INVENTION

A pharmaceutical drug delivery system having a base comprising at least two inlets, an outlet and a passive mixing chamber having micro pin fins with heights in the range of 10 to 100 μm characterized in that the base is selectively coated with nanostructures which are made of a material different than the material of the base, such that the base comprises a plurality of regions $R_1$ to $R_N$ each having a different nanostructure coating intensity, and such that a surface tension gradient is established among regions $R_1$ to $R_N$ for promoting fluid flow towards the outlet. The present invention further proposes a method for obtaining a pharmaceutical drug delivery system having a base, at least two inlets, an outlet and a passive mixing chamber having micro pin fins with heights in the range of 10 to 100 µm, which method comprises the steps of forming a base comprising at least two inlets, an outlet and a passive mixing chamber having micro pin fins; and selectively coating the base with nanostructures made of a material which is different than the material of the base, such that the base comprises a plurality of regions $R_1$ to $R_N$ each having a different nanostructure coating intensity, and such that a surface tension gradient is established among regions $R_1$ to $R_N$ for promoting fluid flow towards the outlet.

BRIEF DESCRIPTION OF THE FIGURES

The figures whose brief explanations are herewith provided are solely intended for providing a better understanding of the present invention and are as such not intended to define the scope of protection or the context in which the scope is to be interpreted in the absence of the description.

DETAILED DESCRIPTION OF THE INVENTION

Referring now to the figures outlined above, the present invention proposes a micro electro mechanical system (MEMS) which is a drug delivery system, which has features of passive reagent mixing with enhanced micro structures.

Figure 1:
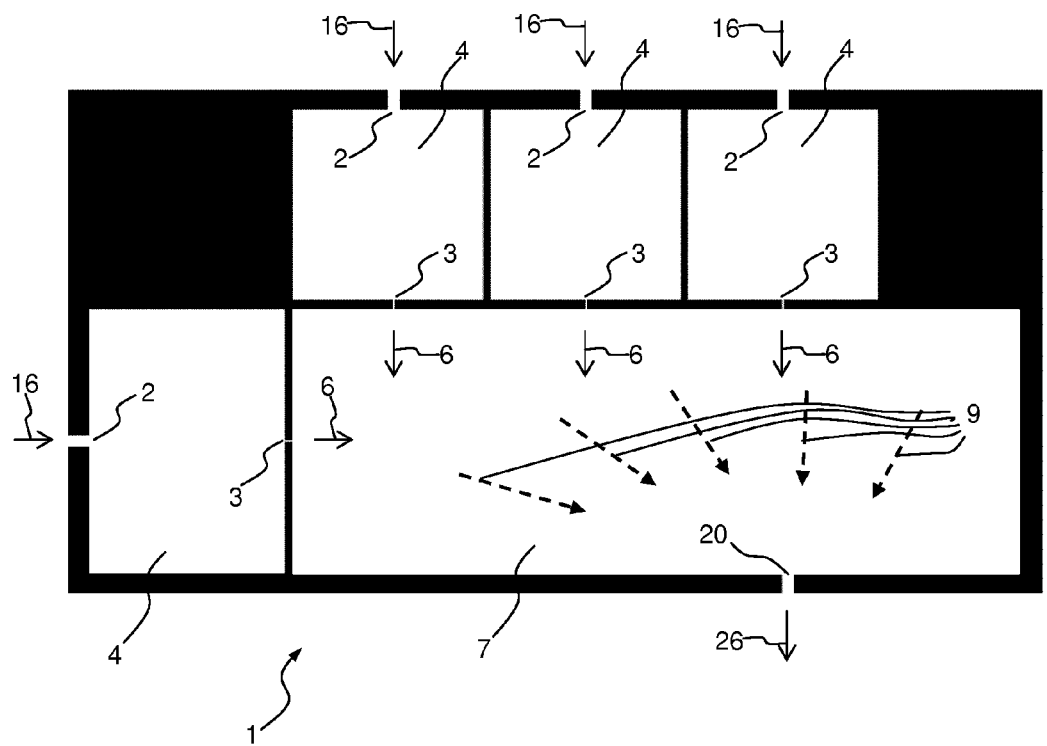
FIG. 1 shows a plan view of an embodiment of a base for the drug delivery system according to the present invention.

FIG. 1 shows an embodiment of base (1) of a drug delivery system according to the present invention. Base (1) comprises a plurality of fluid transferring paths i.e. which are inlets (2), passive mixing chamber (7) having micro pin fins (8) and outlet (20).

In a preferred embodiment, a chamber into which the fluids to be mixed are introduced are primary chambers (4). Primary chamber (4) has at least one inlet (2) portion for introduction of fluids into the primary chamber; and microchannel (3) for transferring fluids into passive mixing chamber (7). Microchannel (3) preferably comprises a micro-orifice (not shown) for mitigating cavitating flow to enhance mixing. Fluid flow directions on base (1) are basically shown with arrows (6), introduction or injection of fluids into the system through inlets (2) is basically shown with arrows (16), and fluid mixture outlet (20) from the device is basically shown with arrow (26). Base (1) for the drug delivery system according to the present invention is preferably prepared in one piece.

In accordance with mixing sequence necessities for certain drug compositions, before being transferred into passive mixing chamber (7), fluids in primary chamber (4) can be further transferred through microchannel (3) into a subsequent chamber (not shown) for further mixing with a fluid transferred from another primary chamber (4).

Any chamber is preferably monitored in terms of pH by using a sealed pH probe (not shown). Wet portions of the base i.e. fluid transferring paths (2, 3) to be subjected to fluids can be heated to obtain preferred temperatures for aimed mixing operations.

According to the present invention, base (1) comprises at least one passive mixing chamber (7) comprising micro pin fins (8) with heights of 10-100 µm to enhance passive mixing of fluids by generating turbulence within flowing fluid mixture. The turbulence provides an evenly distribution of temperature and concentrations inside passive mixing chamber (7). Micro pin fins (8) also enhance heat transfer to chamber (4) from a heater (not shown) adjacent with base (1). Considering the plan views on FIGS. 1 and 2 show the upper side of the base (1), the heater can preferably be mounted to the lower side of base (1) which is the opposite side of the upper side.

Figure 2:
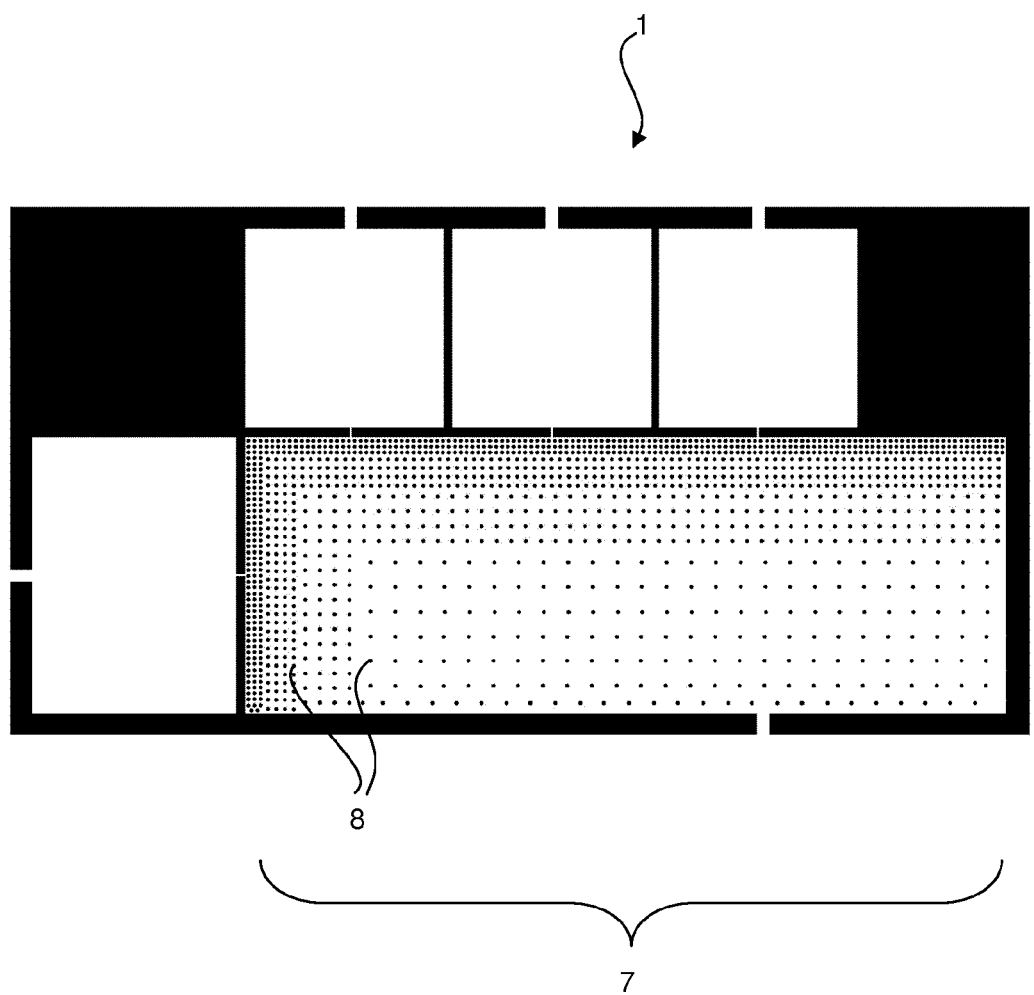
FIG. 2 shows a plan view of the embodiment of FIG. 1, wherein micro pin fins in the passive mixing chamber are emphasized.

FIG. 2 shows a plan view of the embodiment of FIG. 1, wherein a preferred distribution for micro pin fins (8) on base (1) is emphasized. Also a homogeneous distribution of micro pin fins (8) is possible.

For implementation and fabrication of a base for a drug delivery system according to the present invention, a machinable material known for the skilled person in the art of microfabrication e.g. silicon, PDMS (polydimethyl siloxane), SU-8, glass, metals and alloys; and preferably silicon, SU8 or PDMS can be selected. Base (1) can be fabricated by a microfabrication method such as micromilling, soft lithography, molding, IC (integrated circuit) fabrication methods including lithography, DRIE (deep reactive ion etching), and deposition techniques for keeping the dimensions of the base in micro scale.

Figure 3:
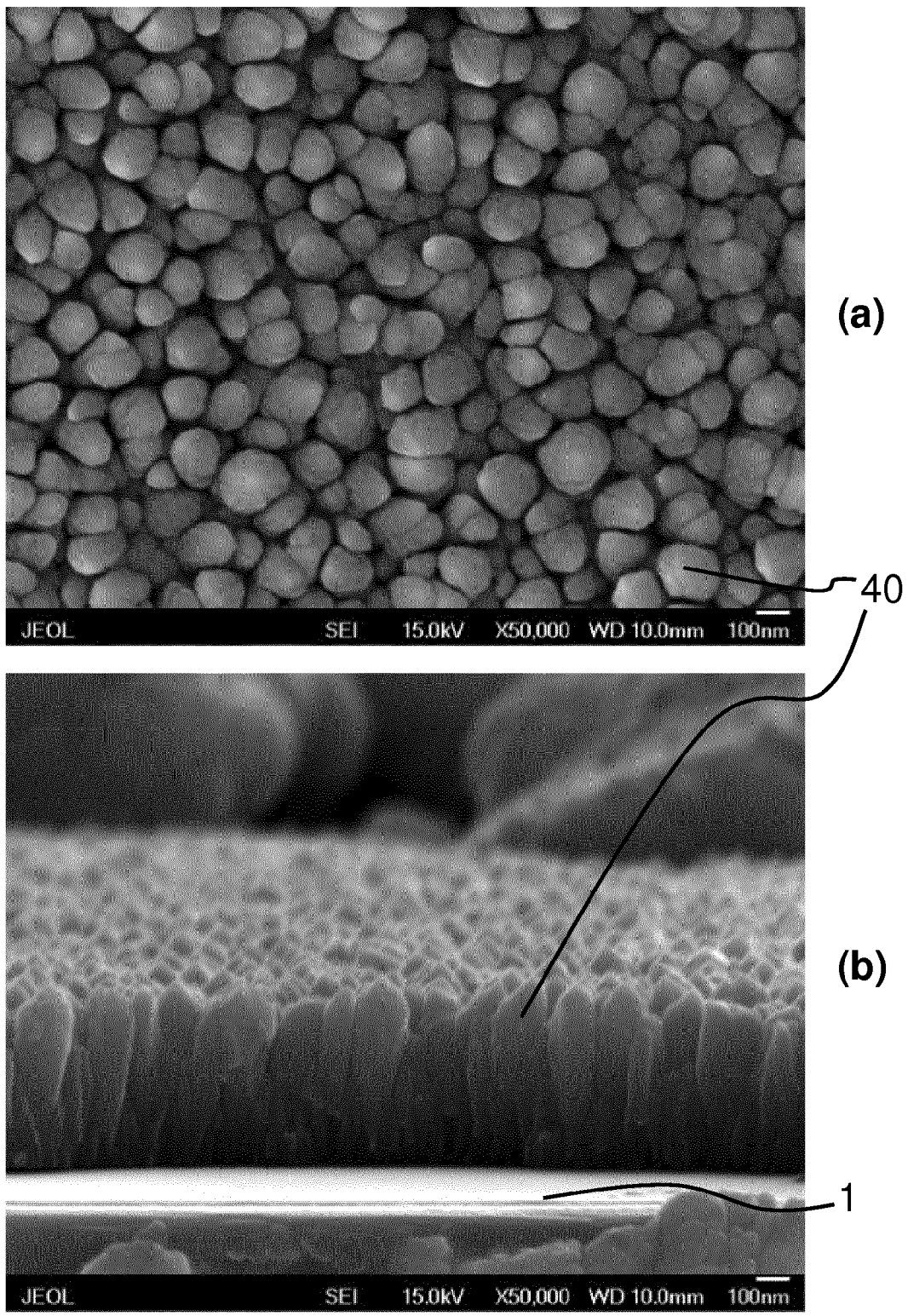
FIG. 3 shows scanning electron microscope (SEM) photographs of the base for a drug delivery system according to the present invention, wherein the base is provided with basically perpendicular nanostructures; (a) shows the plan view of the base surface, and (b) shows a cross-section thereof.
Figure 5:
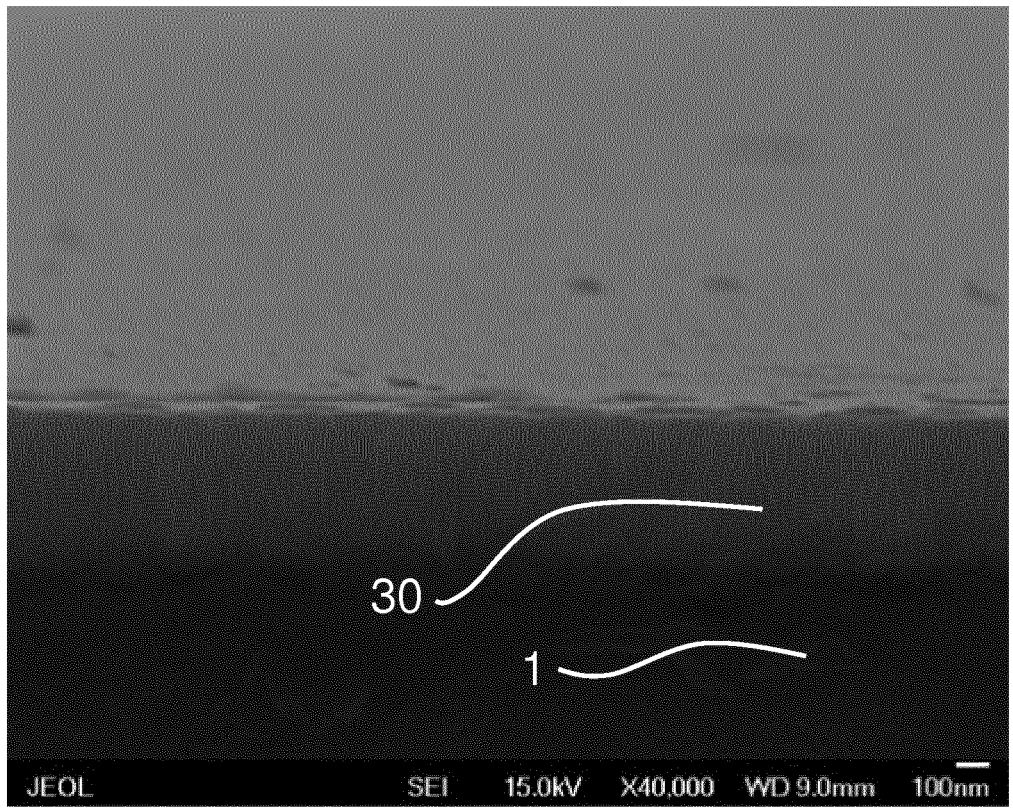
FIG. 5 shows a representative SEM photograph of a cross-section of a base for a drug delivery system according to the present invention, wherein the base is nano-film-coated.

The surface tension gradient accordingly promotes/propels fluid flow in a chamber towards outlet (20) even without requiring any external mechanical work e.g. pumping. A nanostructure may be nano-film (30) as shown in FIG. 5, or a geometrical shape, preferably nano-rod (40) as shown in FIG. 3 integrated on the base, the form of which can be considered as basically cylindrical.

As mentioned above, the distribution of nanostructures varies throughout the base, so that the intensity or distribution of nanostructures is gradual throughout the fluid flow direction. The direction, on which the surface tension gradient promotes the fluid flow, is basically represented on FIG. 1 with arrows (9). Additionally, at regions on base (1) in proximinity of outlet (20), the nanostructures intensity can be either in its minimum or maximum extent. Whether the intensity in proximity of outlet (20) is minimum or maximum, is to be chosen in accordance with production material of base (1), that of the nanostructures, and the fluids to be mixed in the drug delivery system.

Base (1) is selectively coated with nanostructures which are made of a material different than the material of the base, such that base (1) comprises a plurality of regions $R_1$ to $R_N$ with varying nanostructure coating intensities, and such that a surface tension gradient is established among regions $R_1$ to $R_N$ for promoting fluid flow towards outlet (20). The nanostructure coating material is made of a material selected from a group consisting of silicon, polydimethyl siloxane, SU-8, glass, metals and metal alloys.

Figure 4:
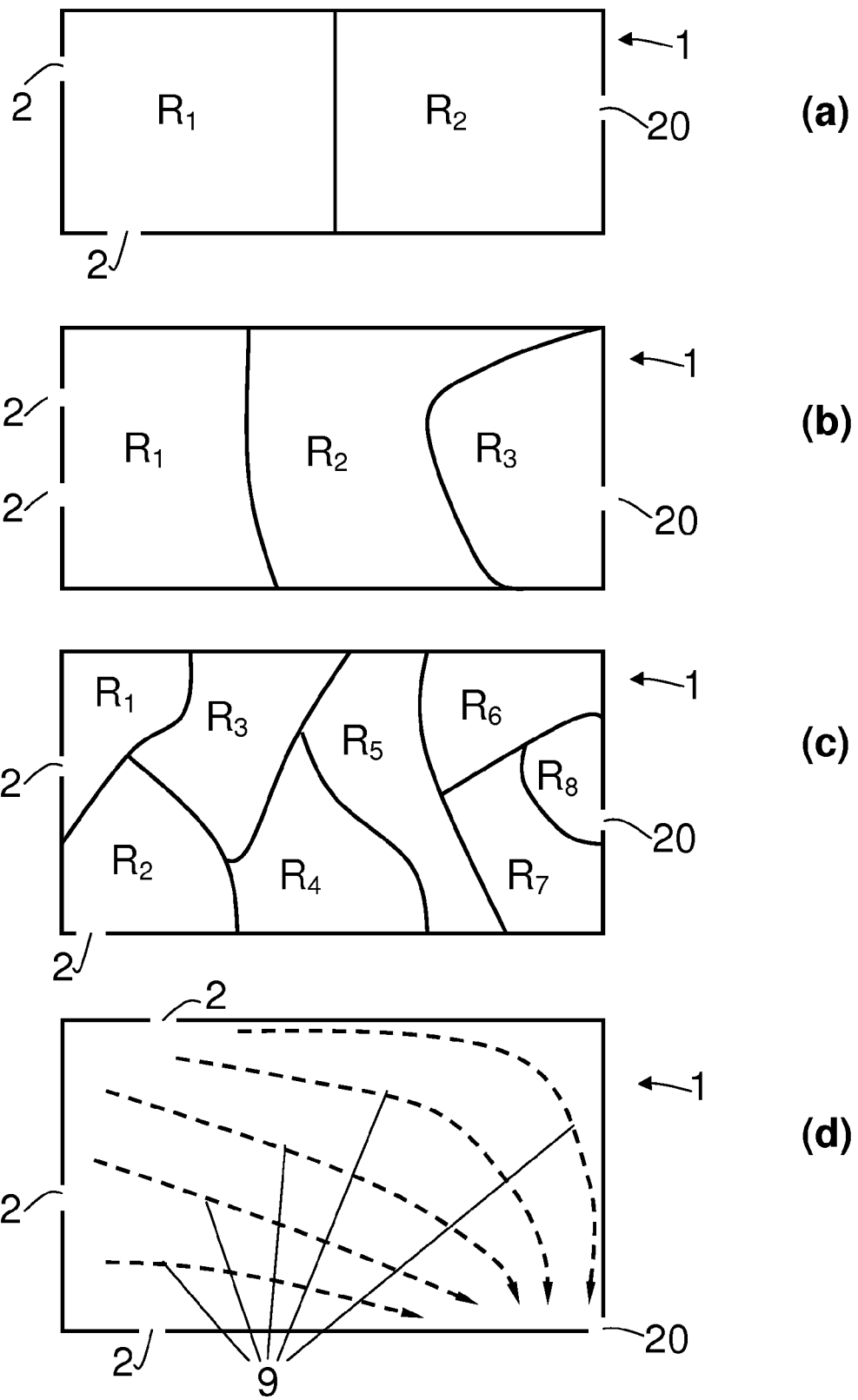
In FIG. 4, (a), (b) and (c) schematically show regions on base embodiments for a drug delivery system according to the present invention. (d) schematically shows a surface tension gradient for promoting fluid flow towards the outlet of an embodiment of a base for a drug delivery system according to the present invention.

In FIG. 4, (a), (b) and (c) schematically show how base (1) divides into regions ($R_1$ to $R_N$), where $1<N$ and N denotes the number of regions with varying nanostructure coating intensities. The intensity of nanostructure coating on a certain region is equal to zero where a unit area (1 µm²) on the region does not comprise any nanostructure, and equal to 1 where a unit area on the region is fully covered with nanostructures. The SEM photograph given in FIG. 3 shows nano-rods (40) coated region with a nanostructure coating intensity of 1, and the representative SEM photograph given in FIG. 5 shows nano-film (30) coated region with a nanostructure coating intensity of 1. For obtaining a surface tension gradient in the drug delivery system according to the present invention, nano-film (30) may have a thickness ranging between 50-1500 nm.

The surface tension gradient promoting the fluid flow towards outlet (20) is obtained at the liquid-solid interface along the pre-determined fluid flow direction, since the surface tension behavior between liquids and solids in contact with the liquids vary for material choices for nanostructures and base i.e. solid materials. The minimum intensity may be apprehended as absence of nanostructures in a region on the base, either in proximal or distal regions to outlet (20).

Known deposition techniques for nano-scale fabrications such as GLAD (Glancing Angle Deposition), CVD (Chemical Vapor Deposition) and PVD (Physical Vapor Deposition) are suitable for obtainment of such nanostructures. The base which is at least partly provided with nanostructures of gradual intensity, shape and layout profiles throughout the base can preferably be obtained by GLAD.

Nano-rods for a base for a drug delivery system according to the present invention have diameters of 50-150 nm and more preferably 75-125 nm; and heights of 500-3000 nm, more preferably 1000-1500 nm for obtaining sufficient fluid guidance effect by adjusting their intensity thus a surface tension gradient throughout the base occurs.

FIG. 3 shows scanning electron microscope (SEM) photographs of the base, wherein the base is provided with basically perpendicular nano-rods as nanostructures; (a) shows the plan view of the base surface, and (b) shows a cross-section thereof. The nano-rods can also be inclined with respect to the base surface for obtaining a nanostructure covered base for a drug delivery system according to the present invention.

In a preferred embodiment according to the present invention, outlet (20) is located in proximity of a distal corner of the base with regard to inlet (2) as schematically exemplified in (d) of FIG. 4.

The drug delivery system according to the present invention may have reduced pressure. Such system comprises a cover (not shown) for protecting base (1) from outer factors. When the cover is connected to base (1), microchannels (3) and chambers (7, 4) define an 'inside' of the drug delivery system; thus inlets (2) and outlet (20) remain as mere openings of the drug delivery system connecting the inside of the drug delivery system to the atmosphere. When the inlets and the outlet are sealed, the system becomes a closed, isolated system. By reducing the pressure (applying vacuum) inside the system before the isolation, the pressure inside the drug delivery system remains reduced compared to the atmospheric pressure until the first use of the drug delivery system. Even though it is not an essential feature of the present invention, reduced pressure inside the system facilitates feeding fluids by causing suction into the system and particularly towards passive mixing chamber (7).

The cover is preferably optically transparent so that the fluids in the system and the drug delivery to the patients can be visually spectated. Therefore, the cover is preferably a thin layer made of a transparent solid material e.g. Pyrex, sealed to base (1).

The final mixture can be collected from outlet (20) using an injector (not shown), yet the microfluidic drug delivery system according to the present invention preferably comprises a secondary chamber (not shown) connected with passive mixing chamber (7) for storing the final fluid mixture upon leaving passive mixing chamber (7) through outlet (20). The final mixture can be taken through an opening on the secondary chamber, for instance by using an injector.

A preferred embodiment of the drug delivery system according to the present invention comprising the following components was used as prototype:
  base (1),
  a cover preferably of a transparent material (here, Pyrex),
  inlet pipes for feeding fluids to be mixed into the system through inlets (2),
  an outlet pipe for receiving fluid mixture from the system through outlet (20),
  a secondary chamber for reserving the mixture upon exiting through the outlet pipe,
  a heater,
  a controller board for temperature control of the system,
  a battery,
  an outer casing for holding the parts, preferably made of transparent plastic,
  syringes for feeding and collecting fluids through each inlet pipe and from the outlet pipe,
  microvalves, preferably piezo microvalves for each inlet and outlet.

The mixing performance of the microfluidic drug delivery system of the above prototype was tested using Bradford reagent (obtained from Sigma Aldrich under the product name B6916) and deionized water, and the absorbance difference results has shown that the mixing performance of the system is found substantial and satisfactory.

Also a method is proposed for producing a pharmaceutical drug delivery system having base (1) comprising at least two inlets (2), outlet (20) and passive mixing chamber (7) having micro pin fins (8) with heights in the range of 10 to 100 µm which method comprises the following steps:
  a—Forming base (1) comprising at least two inlets (2), outlet (20) and passive mixing chamber (7) having micro pin fins (8) with heights of 10-100 µm, wherein the base is formed using a microfabrication technique selected from the list consisting of micromilling, soft lithography, molding, lithography, deep reactive ion etching, and deposition techniques; here, the base is made of a machinable material selected from the list consisting of silicon, polydimethyl siloxane, SU-8, glass, metals and alloys;
  b—Selectively coating of the base with nanostructures which are made of a material different than the material of the base, such that base (1) comprises a plurality of regions $R_1$ to $R_N$ with varying nanostructure coating intensities, and such that a surface tension gradient is established among regions $R_1$ to $R_N$ for promoting fluid flow towards outlet (20); here, the nanostructure covering is performed using a technique selected from the list consisting of glancing angle deposition, chemical vapor deposition, and physical vapor deposition;

The proposed design and method is promising since it is more compact than commercial pumps in terms of the size and still generates similar flow rates compared to the other micropumps. Furthermore, the design has no moving parts. This kind of actuation could be a significant alternative for more common techniques such as electromechanical, electrokinetic, and piezoelectric actuation and could assist to the flows of reagents due to pressure difference between the inlet and into desired location on the system.

The heater is preferably controlled by a controller circuit. The controller circuit is preferably connected to the casing fed by batteries, preferably located adjacent with the casing, and even more preferably on the lower surface of the base.

A standard control board such as a pair of Suboard II controller is supplied for the use in a prototype according to the preferred embodiment. In order to control the mixing process in the system, data provided by temperature sensors and the progress time may preferably be displayed on a display such as an LCD screen of the controller circuit. Analog data provided by temperature sensors is converted into digital data by a microcontroller in order to see heating process on the display in the control of heating process. The microcontroller is supplied with battery power, and battery power can also be used for supplying a control relay between the heater and the power supply thereof. By designing a specific drug preparation procedure, such microcontroller circuits and related components are suitable to be programmed according to corresponding specifications.

A heater circuit for a drug delivery system according to the present invention may comprise several resistors including bias resistors, a thermistor, a diode and a FET transistor. The heater circuit provides required average temperature throughout the microfluidic drug delivery system. The heating process is controlled via a microcontroller. The heater circuit is connected to the microcontroller and obtains necessary voltage from the controller board. A display such as a LED indicator can be added for indication of the temperature within the device. The change in the bias resistors can be applied to obtain a set point as a higher limit for the temperature. Solid state temperature sensors are suitable for the system. Such sensors enable temperature measurements between −55 and 150° C. for control applications. A temperature sensor can be used for determining minimum, average, and differential temperatures. Temperature sensors for the device convert temperature input into proportional current output so that one can see the actual temperature level and even control it by connecting the temperature sensor to the microcontroller. In a preferred embodiment for the drug delivery system according to the present invention, at least one of such sensors is integrated with the device. Temperature values due to the heat supplied by the heater are to be measured by these temperature sensors.

The presence of micro pin fins (8) increases also the heat transfer surface area thus enhancing heat transfer between the base and the fluids inside the chamber.

A packaging for the device protects the base from outer contaminants such as dust and fluids. If a heater is attached to the device of the present invention, the packaging material should be thermally conductive e.g. a metal or alloy thereof for facilitating the heat transfer from the outside of the packaging. Obviously, the melting point of the packaging material should be higher than the temperatures provided by the heater.

CAD (computer-aided design) models can be prepared before the implementation in order to accelerate the planning and the fabrication process of the device of the present invention. During the implementation of simplified CAD models, appropriate machine tools such as above mentioned microfabrication methods can be used to fabricate the device.

The present invention enables mobility in a practical and economical manner due to its size and disposable coverage. The drug delivery process is highly safe due to control of the quantity of reagents and the heating operation.

The drug delivery system of the present invention which is a micro electro mechanical system (MEMS) further provides an improved device featuring homogenous mixing process of multiple reagents, heating process, and controllability. Conveying of reagents is independent of any external device and independent of power source. This group of objects is achieved by means of surface tension gradients on the base in consequence of non-homogenous distribution of nanostructures, and reduced pressure within the device. Effective heating as a result of enhanced surface area with pin fins promoting turbulation thus mixing provides significant advantages over microfluidic drug delivery systems of the prior art.

Thus the present invention brings passive conveying, effective mixing, heating and controlling all the processes together in one device. Further, it does not require any external power source and is relatively cheap in comparison with alternative drug delivery systems such as transdermal ones. Homogenous mixing of the reagents is achieved in an improved manner.

By limiting the unnecessary amounts of the reagents in quantity, the side effects that are caused by the overdose of reagents are diminished. Drugs are administered to patients with just sufficient amounts of the reagents in a controlled and safe fashion. The drug delivery system of the present invention exploits Micro Electro Mechanical System (MEMS) technology to address to the requirement for an autonomous, effective, and compact drug delivery system. Hence, the present invention overcomes the aforementioned deficiencies in the prior art.

The invention claimed is:

1. A pharmaceutical drug delivery system having a heater, a base comprising at least two inlets, an outlet and a passive mixing chamber having micro pin fins with heights in the range of 10 to 100 µm, wherein the micro pin fins enhance heat transfer from the heater and promote passive mixing by generating turbulence within a flowing fluid mixture thereby providing an even distribution of temperature and concentration within the passive mixing chamber, wherein a surface portion of the base is coated with a coating material different from a material of said surface portion of the base, wherein a height of said coating material from said surface portion of the base is in nano scale, wherein distribution of said coating material throughout said surface portion of the base varies from the inlets towards the outlet such that the surface portion of the base comprises a plurality of regions $R_1$ to $R_N$ each having a different distribution of the coating material relative to each other, thereby establishing a surface tension gradient among regions $R_1$ to $R_N$ for promoting fluid flow towards the outlet.

2. The pharmaceutical drug delivery system according to claim 1, wherein the base further comprises a primary chamber having one or more microchannel(s) for conveying fluid into the passive mixing chamber.

3. The pharmaceutical drug delivery system according to claim 1, wherein the base is made of a material selected from a group consisting of silicon, polydimethyl siloxane, SU-8, glass, metals and metal alloys.

4. The pharmaceutical drug delivery system according to claim 1, wherein the coating material provided onto the surface portion of the base is selected from a group consisting of silicon, polydimethyl siloxane, SU-8, glass, metals and metal alloys.

5. The pharmaceutical drug delivery system according to claim 1, wherein the coating material provided onto the surface portion of the base is in form of nano-rods having diameters of in the range of 50 nm to 150 nm and heights in the range of 500 nm to 3000 nm from the surface portion of the base on which the coating material is provided.

6. The pharmaceutical drug delivery system according to claim 1, wherein the coating material provided onto the surface portion of the base is in form of nano-rods having diameters of 75 nm to 125 nm and heights of than 1000 nm to 1500 nm from the surface portion of the base on which the coating material is provided.

7. The pharmaceutical drug delivery system according to claim 1, wherein the coating material provided onto the surface portion of the base is a nano-film having a thickness in the range of 50-1500 nm.

8. The pharmaceutical drug delivery system according to claim 1 wherein the system further comprises a cover made of an optically transparent material.

9. A pharmaceutical drug delivery system according to claim 1, wherein the drug delivery system comprises a secondary chamber connected with the passive mixing chamber for storing fluid upon leaving the passive mixing chamber through the outlet.

10. The pharmaceutical drug delivery system according to claim 1, wherein the base further comprises a primary chamber having one or more microchannel(s) for conveying fluid into a subsequent chamber.

11. The pharmaceutical drug delivery system according to claim 10, wherein the one or more microchannel(s) comprises a micro-orifice for mitigating cavitating through flow adapted to enhance mixing.

12. A method for producing a pharmaceutical drug delivery system having a heater, a cover and a base comprising at least two inlets, an outlet and a passive mixing chamber having micro pin fins with heights in the range of 10 to 100 µm; the method comprising the steps of: a—forming of a base comprising at least two inlets, an outlet and a passive mixing chamber having micro pin fins with heights in range of 10 to 100 µm; wherein the micro pins enhance heat transfer from the heater and promote passive mixing by generating turbulence within a flowing fluid mixture thereby providing an even distribution of temperature and concentration within the passive mixing chamber, b—providing a surface portion of the base with a coating material which is different from the material of the base, wherein a height of the coating material from the surface portion of the base is in nano scale, wherein distribution of the coating material throughout the surface portion of the base varies from the inlets towards the outlet, such that the surface portion of the base comprises a plurality of regions $R_1$ to $R_N$ each having a varying distribution of the coating material relative to each other, thereby establishing a surface tension gradient among regions $R_1$ to $R_N$ for promoting fluid flow towards the outlet.

13. The method according to claim 12, wherein the base is formed using a microfabrication technique selected from the list consisting of micromilling, soft lithography, molding, lithography, deep reactive ion etching, and deposition techniques.

14. The method according to claim 12, wherein a distribution of the coating material provided onto the surface portion of the base is performed either by glancing angle deposition, chemical vapor deposition or by physical vapor deposition.

15. The method according to claim 12, wherein the method further comprises the step of isolating the drug delivery system and applying vacuum within the passive mixing chamber.

* * * * *